United States Patent [19]

Pirali et al.

[11] Patent Number: 4,692,333

[45] Date of Patent: Sep. 8, 1987

[54] ANTIMICROBIAL AND ANTITUMOR ANTIBIOTIC M 9026 AND ITS PURE INDIVIDUAL FACTORS 1, 2, AND 3 AND MICROBIAL PROCESS FOR PRODUCTION THEREOF

[75] Inventors: Giorgio Pirali, Saronno; Maria Grandi, Reggio Emilia; Hermes Pagani, Sesto San Giovanni; Manuela Paternoster, Meda; Giorgio Tamoni, Milan; Giovanni Cassani, Pavia, all of Italy

[73] Assignee: Gruppo Lepetit S.p.A., Milan, Italy

[21] Appl. No.: 520,088

[22] Filed: Aug. 4, 1983

[30] Foreign Application Priority Data

Aug. 26, 1982 [GB] United Kingdom ................. 8224512

[51] Int. Cl.$^4$ ..................... A61K 35/74; C12D 13/02; C12N 1/20; C12R 1/29
[52] U.S. Cl. .................................... 424/122; 435/129; 435/170; 435/253; 435/867
[58] Field of Search ............... 435/867, 128, 129, 170, 435/169, 253; 424/122

[56] References Cited

U.S. PATENT DOCUMENTS 3,511,909 5/1970 Luedemann et al. ............... 435/170
4,367,287 1/1983 Waitz et al. .......................... 435/867

FOREIGN PATENT DOCUMENTS 0023909 2/1980 Japan .................................... 435/867
6122392 9/1981 Japan .................................... 435/867

OTHER PUBLICATIONS

U.K. Patent Application No. 2022573, published 12-19-79, Keller-Juslen, et al.

*Primary Examiner*—Thomas G. Wiseman
*Assistant Examiner*—Elizabeth C. Weimar
*Attorney, Agent, or Firm*—Stephen L. Nesbitt

[57] ABSTRACT

New antibiotic substances arbitrarily designated M 9026 complex, antibiotic M 9026 factor 1, antibiotic M 9026 factor 2, and antibiotic M 9026 factor 3, produced by fermentation of a strain of the Micromonospora genus. The antibiotics of the invention are antimicrobial and antitumor agents.

18 Claims, 11 Drawing Figures

ANTIMICROBIAL AND ANTITUMOR ANTIBIOTIC M 9026 AND ITS PURE INDIVIDUAL FACTORS 1, 2, AND 3 AND MICROBIAL PROCESS FOR PRODUCTION THEREOF

The present invention is directed to a group of antibiotic substances arbitrarily designated as antibiotic M 9026 complex, and the pure fractions designated antibiotic M 9026 factor 1, factor 2 and factor 3, which are isolated from antibiotic M 9026 complex, to the fermentation process for the production of these antibiotic substances as well as to the separation of the complex into the single fractions.

One object of this invention is therefore antibiotic M 9026 complex which is obtained by culturing a hitherto undescribed strain which has been taxonomically characterized as a species of the Micromonospora genus and represents a further object of this invention.

A culture of this strain, which was collected at Nangal (India), has been deposited under the provision of the Budapest Treaty on Jul. 30, 1982, with the Agricultural Research Culture Collection (NRRL), 1815 N. University Street—Peoria, Ill. 61601 U.S.A., where it was accorded the accession number NRRL 15,118. Another object of this invention is the antibiotic M 9026 factors 1, 2, and 3 isolated and separated from the fermentation broth and/or micelial mass of the Micromonospora culture.

For ease of description and in view of similar utility of antibiotic M 9026 complex, antibiotic M 9026 factor 2, and antibiotic M 9026 factor 3, in the following disclosure, when dealing with the activities or the preparation and purification techniques, the terms "M 9026 compounds" or "M 9026 antibiotics" refer to a compound selected from antibiotic M 9026 complex, antibiotic M 9026 factor 2, and antibiotic M 9026 factor 3.

In vitro, the M 9026 compounds inhibit the growth of certain pathogenic bacteria, especially gram positive, and have been found to be effective in inhibiting the growth of tumoral cells both in in vitro cultures and in in vivo experiments in mammals.

The characteristics of the strain Micromonospora sp. NRRL 15,118 are given in the following paragraphs:

Morphology

Strain Micromonospora sp. NRRL 15,118 grows well on various nutrient agar. In oatmeal agar the colonies are raised with a diameter of 2-3 mm, show regular contours and ridged surfaces. Aerial mycelium is always absent. On microscopic examination the mycelium appears to be long, branched, and regular in diameter (0.6 μm). Oval to spherical spores are abundantly produced with a diameter of 0.7-1.0 μm. The sessile spores rise directly from the mycelium and are borne predominantly on simpodially branched sporophores. Observation of spores and sphorophores were made in shaken-broth culture according to Luedemann (Intern. J. Syst. Bact. 21, 240-247, 1971).

Cultural characteristics

Table I reports the cultural characteristics of Micromonospora sp. NRRL 15,118 cultivated on various standard media as suggested by Shirling and Gottlieb (Inter. J. Syst. Bact. 16, 313-340, 1966) and other media recommended by Waksman (The Actinomycetes, Vol. II, the William and Wilkins Co. 1961). These characteristics were determined after 7-14 days of incubation at 30° C.

TABLE I

Cultural characteristics of Micromonospora sp. NRRL 15,118

| Culture Media | Cultural characteristics |
|---|---|
| medium no. 2 (yeast extract-malt agar) | no growth |
| medium no. 3 (oatmeal agar) | moderate growth, rough, light orange brownish surface 12 E 8 |
| medium no. 4 (inorganic salts-starch agar) | abundant growth, rough, orange 11 F 11 |
| medium no. 5 (glycerol-aparagine agar) | poor growth, flat, hyaline to orange light |
| medium no. 6 (peptone yeast extract iron agar) | moderate growth, wrinkled, amber 12 D 9 |
| medium no. 7 (tyrosine agar) | poor growth, flat, hyaline |
| Oatmeal agar (according to Waksman) | abundant growth, rough, orange, blackish surface, moist |
| Hickey and Tresner's agar | abundant growth, wrinkled, brownish |
| Czapeck glucose agar | no growth |
| Glucose asparagine agar | poor growth, flat, hyaline to light orange |
| Nutrient agar | moderate growth, rough, orange 10 T 9 |
| Potato agar | abundant growth, wrinkled, orange, blackish surface, moist |
| Bennett's agar | abundant growth, rough, orange, brownish surface |
| Calcium malate agar | poor growth, flat, hyaline |
| Skim milk agar | moderate growth, rough, orange 11 C 10 |
| Czapeck agar plus CaCO3 | poor growth, flat, hyaline to orange |
| Czapeck agar | poor growth, flat, hyaline to orange |
| Egg agar | poor growth, flat, hyaline to orange |
| Peptone glucose agar | moderate growth, wrinkled orange 11 G 8 |
| Emerson agar | moderate growth, rough, orange, brownish surface |
| Potato plug | no growth |
| Potato plug plus CaCO3 | moderate growth, wrinkled, dusty orange |

Color determination was made by the method of Maerz and Paul (Maerz, A. and M. Reg. Paul 1950. A dictionary of colors, 2 nd Ed., Mc Grow-Hill Book Company, Inc. New York). Culture media numbers, when indicated, refer to those described by Shirling and Gottlieb (Intern. J. Syst. Bact. 16, 313-340, 1966).

Table II reports the utilization of carbon sources determined on the medium described by Luedemann (Inter. J. Syst. Bact. 21, 240-247, 1971), while Table III reports the physiological characteristics of the strain Micromonospora sp. NRRL 15,118.

TABLE II

| Utilization of carbon sources | |
|---|---|
| Carbon sources | Utilization |
| Arabinose | + |
| Xylose | + |
| Glucose | + |
| Fructose | ± |
| Mannose | + |
| Mannitol | − |
| Inositol | − |
| Rhamnose | − |
| Sucrose | + |
| Lactose | + |
| Raffinose | + |
| Cellulose | − |
| Salicin | − |

TABLE II-continued

| Utilization of carbon sources | |
|---|---|
| Carbon sources | Utilization |
| Melibiose | + |
| Galactose | + |
| Ribose | − |
| Dulcitol | − |
| Glycerol | − |
| Cellobiose | + |
| Threalose | + |
| Soluble starch | + |

+ utilization
− lack of utilization
± poor utilization

TABLE III

| Physiological characteristics | |
|---|---|
| Test | Results |
| Starch hydrolysis | positive |
| H$_2$S formation | positive |
| Melanin production | negative |
| Tyrosinase reaction | negative |
| Casein hydrolysis | positive |
| Calcium malate hydrolysis | negative |
| Nitrate reduction | positive |
| Litmus milk | coagulated |
| Gelatin liquefaction | positive |

As with other organisms, the characteristics of the M-9026 producing strain, Micromonospora sp. NRRL 15,118 are subject to variation. For example, artificial variants and mutants of the strain can be obtained by treatment with various known mutagens, such as U.V. rays, X-rays, high frequency waves, radioactive rays, and chemicals such as nitrous acid, N-methyl-N'-nitro-N-nitrosoguanidine, and many others. All natural and artificial variants and mutants which belong to the species of the genus Micromonospora and produce M-9026 antibiotics are deemed equivalent to strain Micromonospora sp. NRRL 15,118 and are contemplated to be within the scope of this invention.

For producing the M 9026 antibiotics, the strain Micromonospora sp. NRRL 15,118 or an equivalent mutant thereof, is cultivated under submerged aerobic conditions in an aqueous nutrient medium containing assimilable sources of carbon, nitrogen and inorganic salts. Said culture medium can be any one of a number of nutrient media usually employed in the fermentation art, however certain media are preferred. Thus, for instance, preferred carbon sources are glucose, starch, maltose, sucrose, galactose, cellobiose, raffinose, fructose, dextrine, molasses and the like. Other useful carbon sources include peanut oil, corn oil, soybean oil, fish oil, and the like.

Preferred nitrogen sources are yeast extracts, aminoacids, casein hydrolysate, beef extract, soybean flour, peptones, and the like. Other useful nitrogen sources include oatmeal, peanut meal, soybean meal, soybean grits, cotton-seed meal, and the like.

Among the inorganic salts which can be incorporated in the culture media, there are the customary soluble salts capable of yielding sodium, potassium, iron, zinc, cobalt, magnesium, calcium, ammonium, chloride, carbonate, sulfate, nitrate, phosphate and the like ions. Essential trace elements necessary for the growth and development of organism should also be included in the culture medium. Such trace elements commonly occur as impurities in the other constituents of the medium in amounts sufficient to meet the growth requirements of the organism.

It may be necessary to add small amounts (e.g. 0.2 ml/l) of an antifoam agent such as polypropylene glycol or silicone derivatives to large scale fermentation media if foaming becomes a problem.

Ordinarily the antibiotic producing strain is pre-cultured in a shake flask, then the culture is used to inoculate jar fermentors for the production of substantial quantities of the M 9026 antibiotics. The medium used for the pre-culture can be the same as that employed for larger fermentations, but other media can also be employed.

The M 9026 producing strain can be grown at temperatures between 25° C. and 37° C. and preferably between 26° and 30° C. The pH of the fermentation mass is generally kept between 6.0 and 8.5. As a customary procedure in aerobic submerged culture processes employing jar fermentors, sterile air is blown through the culture medium. For efficient growth of the organism, the volume of air preferably employed in the production tank is an amount sufficient to maintain a dissolved oxygen concentration greater than 20 per cent.

During the fermentation, antibiotic production can be followed by testing samples of the broth and/or of the extracts of the mycelial mass for antibiotic activity. Organisms known to be sensitive to M 9026 antibiotics are useful for this purpose. An especially useful assay organism is the Staphylococcus aureus.

Other useful test organisms are cells known to be sensitive to the cytotoxic activity of said antibiotics. The bioassay is easily made by agar diffusion method on agar plates or by TLC-autobioassay. Maximum antibiotic activity generally occurs between about 48-72 hours of incubation at the above outlined fermentation conditions.

Following this production under submerged aerobic fermentation conditions, the M 9026 antibiotics can be recovered from the fermentation medium by methods used in the fermentation art, including, for example, extractions with solvents, counter-current extractions, precipitation by non-solvents, column chromatography, thin layer chromatography and the like, and can be further purified by techniques such as crystallization from solvents, liquid chromatography, high performance liquid chromatography (HPLC), reverse-phase HPLC, and the like.

The antibiotics produced during the fermentation of the M 9026 producing organisms are found in the culture broths and or in the mycelial mass. A preferred method for recovering the M 9026 antibiotics is therefore by separate extraction of the filtered fermentation broths and of the mycelial mass.

Thus, after separating the mycelial cake by filtration, antibiotics M 9026 are recovered from the filtrate by extraction with a suitable organic solvent. The extraction is generally carried out after adjusting the pH of the filtrate between 3.5 and 8.5, preferably at 6.0-7.5 and most preferably at about 7. Suitable organic solvents are water-insoluble solvents which dissolve the M 9026 antibiotics; representative examples of them are: lower alkanols, such as methanol, ethanol, propanol and the like, lower haloalkanes, such as chloroform, methylene chloride, chloroethane, and the like; lower alkyl esters, such as ethyl acetate, butyl acetate, propyl acetate, ethyl propionate, ethyl butyrate, and the like; and ketones, such as methyl ethyl ketone and the like. Then the extracts are concentrated to a small volume and the solid which precipitates is recovered by filtration. The precipitation is completed by the addition of a second organic solvent in which the antibiotics M 9026 are not soluble, such as petroleum ether, ethyl ether, or the like.

The mycelial mass, in turn, is washed with water and suspended in one of the above listed solvents suitable for extracting the M 9026 antibiotic substances.

After stirring, the mixture is filtered and the organic solvent is stripped from the filtrate. The pH of the aqueous mixture which remains is then adjusted between 3.5 and 8.5 and preferably between 6 and 7, and extracted as already described for the fermentation broth.

The obtained antibiotics M 9026 can be further purified by known purification techniques, preferably using preparative thin layer chromatography or column chromatography. Absorbant materials such as allumina, silica gel, ion exchange resins such as the Dowex ® resins, cellulose, Sephadex ® and the like can be advantageously used.

A preferred embodiment of the present invention, is the purification of the M 9026 complex using a silica gel chromatography column and eluting with a mixture of a polar solvent, such as a lower alkanol, a halo lower alkane such as chloroform, and a basic agent such as ammonia hydrate.

According to a further preferred embodiment a mixture of chloroform:methanol:ammonia, 66:30:4, is used as the eluting mixture. As used herein, solvent ratios are expressed as volume/volume ratios. The eluted fractions which show antimicrobial activity in the above identified bio-assay test, are pooled and the antibiotic M 9026 complex is recovered according to one of the above identified techniques. Separation of antibiotic M 9026 factor 2 and factor 3, is accomplished by a variety of recognized methods which essentially involve chromatographic procedures. Extraction with solvents, precipitation by solvents, counter current extractions, and the like can also be used.

According to another preferred embodiment, column chromatography is employed; the preferred adsorbent is silica gel and the preferred eluting mixture comprises a polar solvent such as a lower alkanol and a solvent with a low polarity such as a halo lower alkane. A further preferred eluting mixture is chloroform plus methanol at the ratio of 9 to 1 (v/v). The eluted fractions are collected, tested according to the above described bio-assay and pooled accordingly. Antibiotic M 9026 factor 2, and antibiotic M 9026 factor 3 are then recovered from the pooled fractions containing them by one of the procedures described above for the recovery of the M 9026 complex from the extraction mixture.

Physico-chemical properties of antibiotic M 9026 complex and antibiotic M 9026 factors 1, 2, and 3

Antibiotic M 9026 complex

Figure 1:
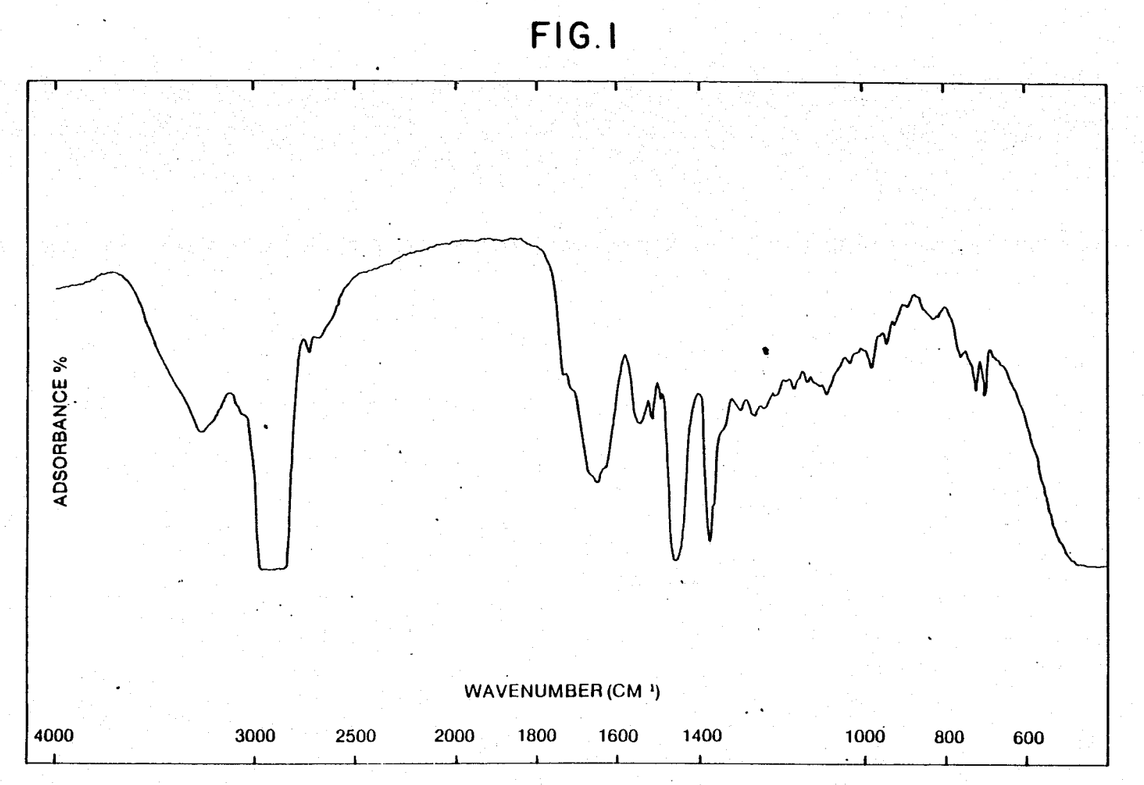

The infrared absorption spectrum in nujol is shown in FIG. 1. The following absorption maxima (cm$^{-1}$) are observed: 3260 (broad), 3060, 2730, 1735, 1720 (shoulder), 1650, 1630, 1545, 1515, 1495, 1300, 1260, 1210, 1170, 1090, 1030, 980, 940, 830, 760, 720, 700.

Figure 2:
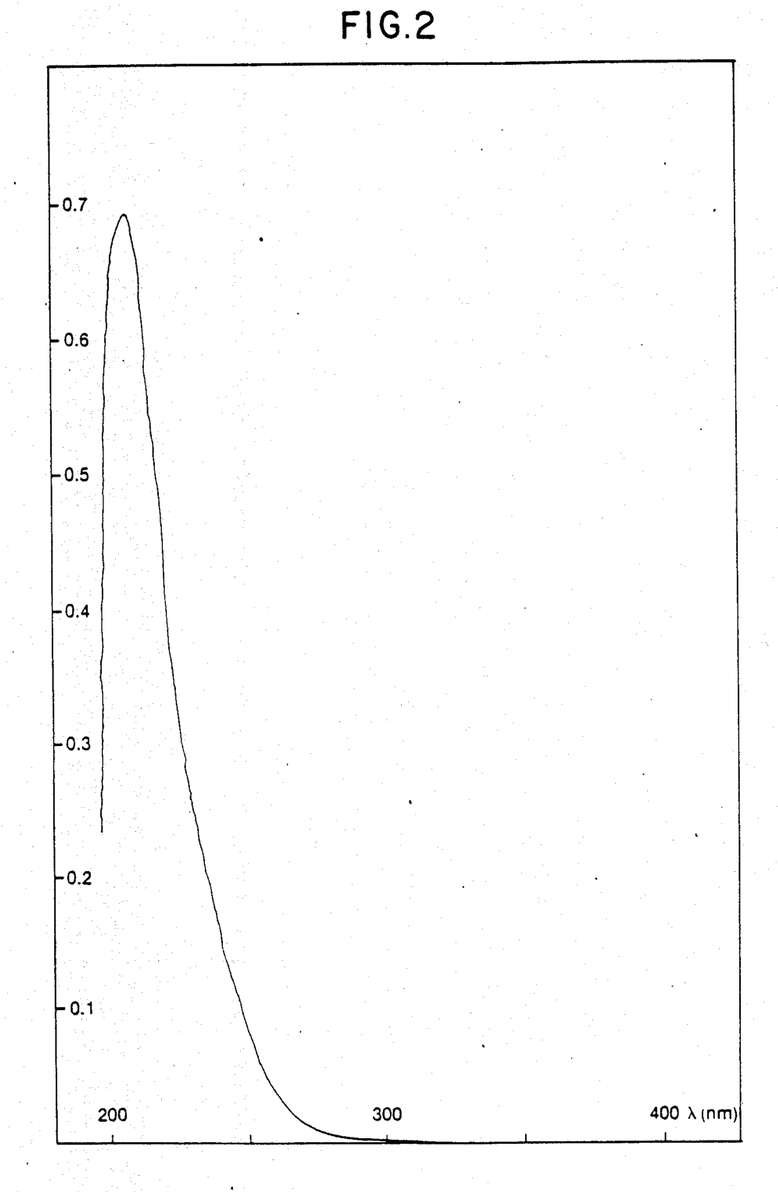

The U.V. spectrum shows a terminal absorption at about 215 nm in methanol and is reported in FIG. 2 of the accompanying drawings.

Antibiotic M 9026 factor 1

Antibiotic M 9026 factor 1 is a crystalline solid with melting point of about 235° C. Is is soluble in chloroform, methanol, less soluble in acetone, hydrocarbons, insoluble in water.

Figure 3:
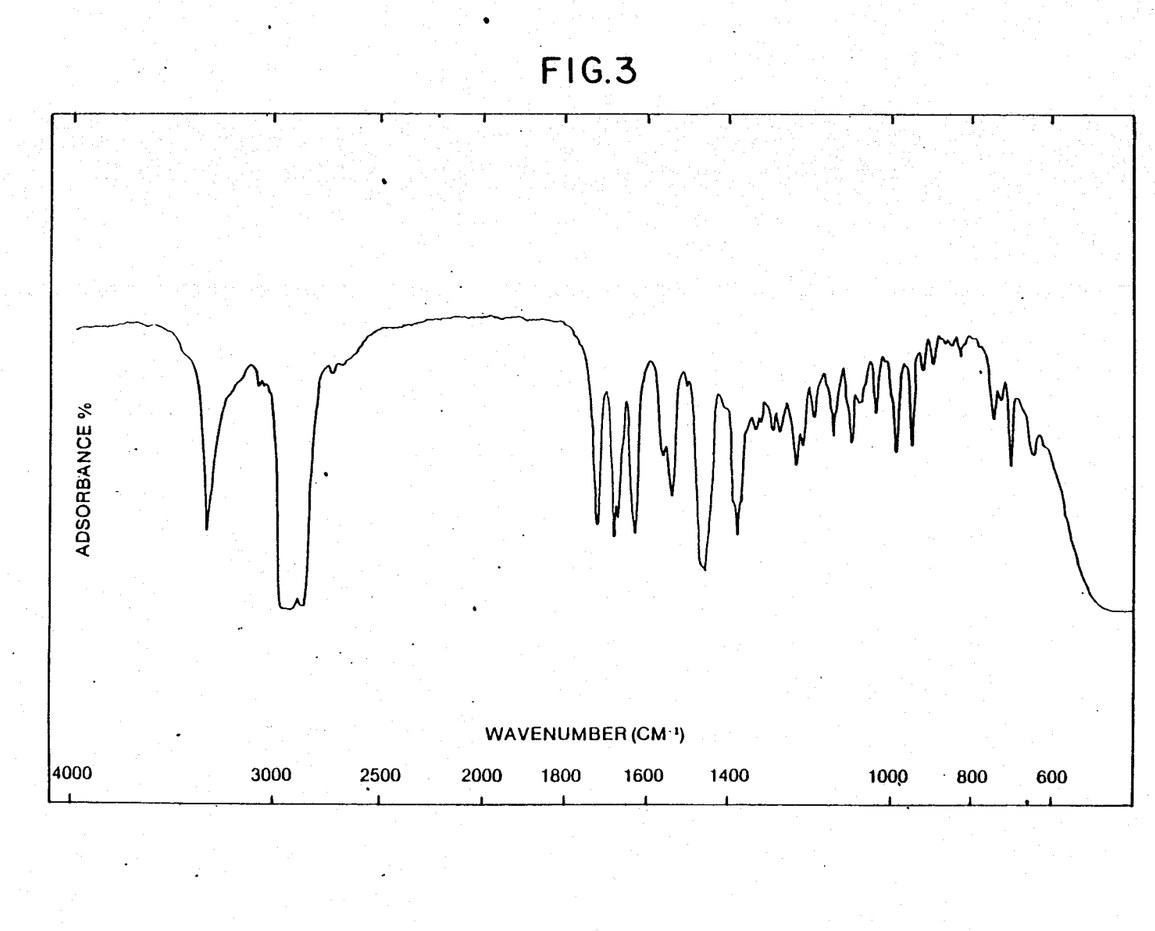

Upon elemental analysis the following approximate percentage composition is obtained: carbon, 68.83%; hydrogen, 8.70%; nitrogen, 5 56%; oxygen (by difference), 16.91%. The infrared absorption spectrum in nujol is shown in FIG. 3 of the accompanying drawings. The following absorption maxima (cm$^{-1}$) are observed in nujol mull: 3670, 3550, 3460, 3320, 3100, 3080, 3040, 2740, 1720, 1660, 1630, 1545, 1500, 1260, 1245, 1220, 1190, 1140, 1090, 1040, 985, 950, 895, 750, 725, 700.

The ultraviolet absorption spectrum shows a terminal absorption at about 215 nm in methanol, essentially (FIG. 2).

Figure 4:
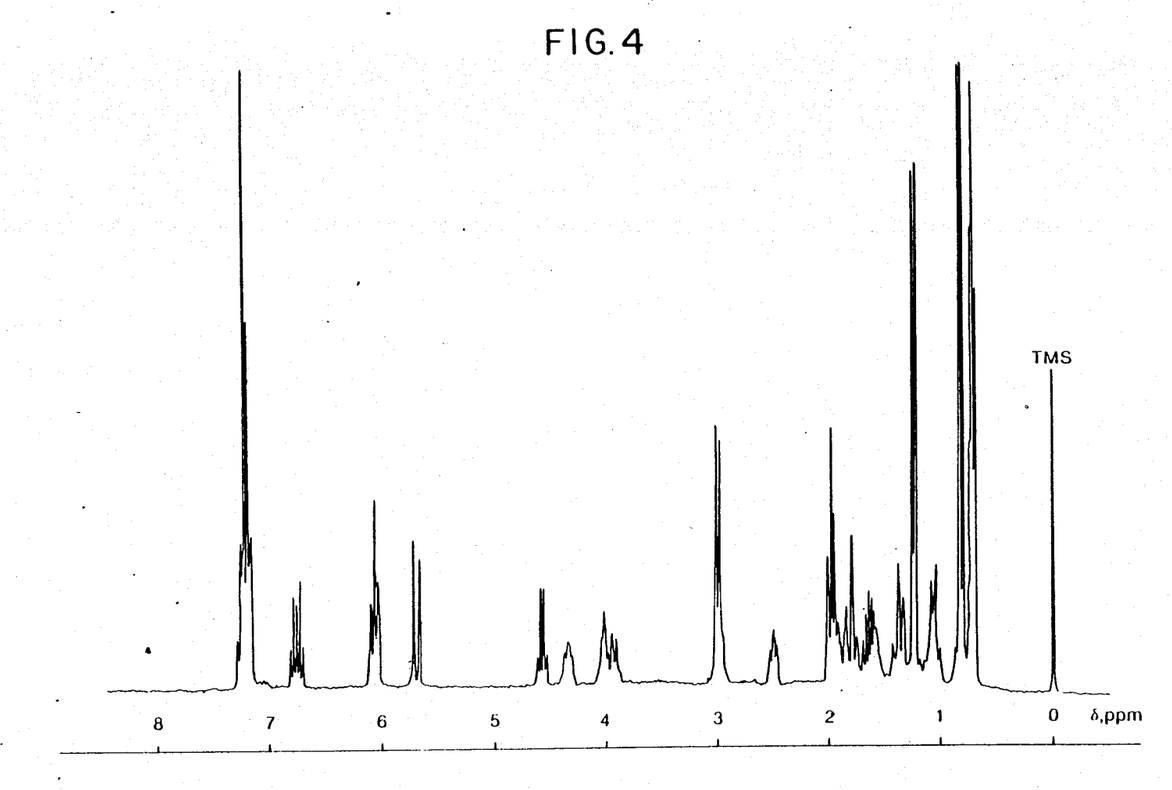

The N.M.R. spectrum, is reported in FIG. 4 and shows the following main peaks: δ0.70–0.73 (2d, 6H, J=6.5), 0.83 (d, 6H, J=7), 1.0–2.0 (m, 4H), 1.06 (m, 1H), 1.24 (d, 3H, J=6.5), 1.5–2.0 (m, 2H), 1.66 (t sept, 1H, J=7.5), 1.98 (ddd, 2H, J=7.5-7.5-1); 2.49 (ddd, 1H, 1H, J=7-10; 2.5), 3.00 (d, 2H; J=7.5), 3.91 (dddd, 1H, J=9; 8; 2.5-9.5), 4.08 (dd, 1H), 4.32 (ddq, 1H; J=2.5-10), 4.57 (dt, 1H; J=8), 5.69 (dt, 1H, J=15), 6.15 (d, 1H), 6.22 (d, 1H), 6.73 (dt, 1H), 7.18 (m, 5H).

Figure 5:
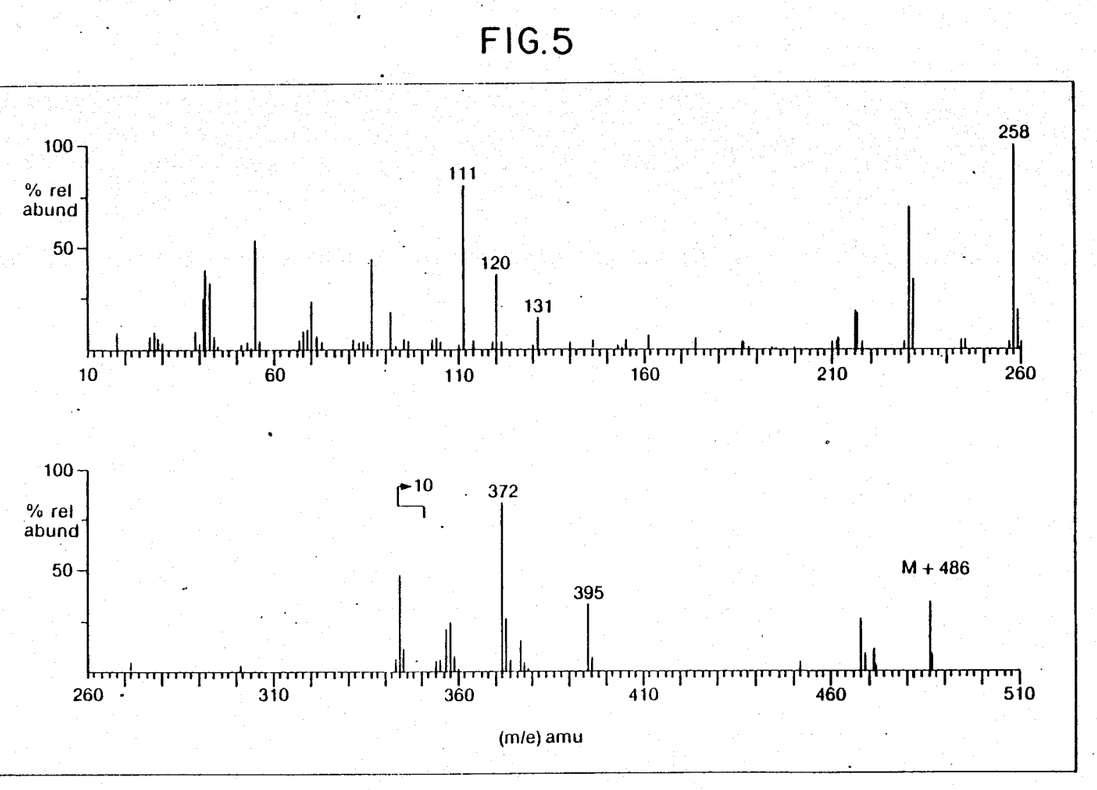

The mass spectrum is shown in FIG. 5. The main peaks are the following (the first number is the rate m/z, and the second, between parenthesis, is the percentage of relative abundance): 486 (35); 91 (18); 111 (81); 120 (37); 216 (18); 217 (19); 230 (70); 231 (34); 258 (100); 344 (48); 372 (8.3); 395 (3.5); 486 (2.6); 471 (1.1).

Antibiotic M 9026 factor 2

Antibiotic M 9026 factor 2 is a white-grey powder with a melting point above 280° C. It is soluble in methanol, ethanol, acetone, ethyl acetate, chloroform; spare soluble in acetonitrile, insoluble in water, petroleum ether, ethyl ether. Upon elemental analysis the following approximate percentage composition (as an average of several analysis) is obtained: carbon, 68.82%; hydrogen 9.04%; nitrogen 5.70%; oxygen (by difference), 17.09%.

Figure 6:
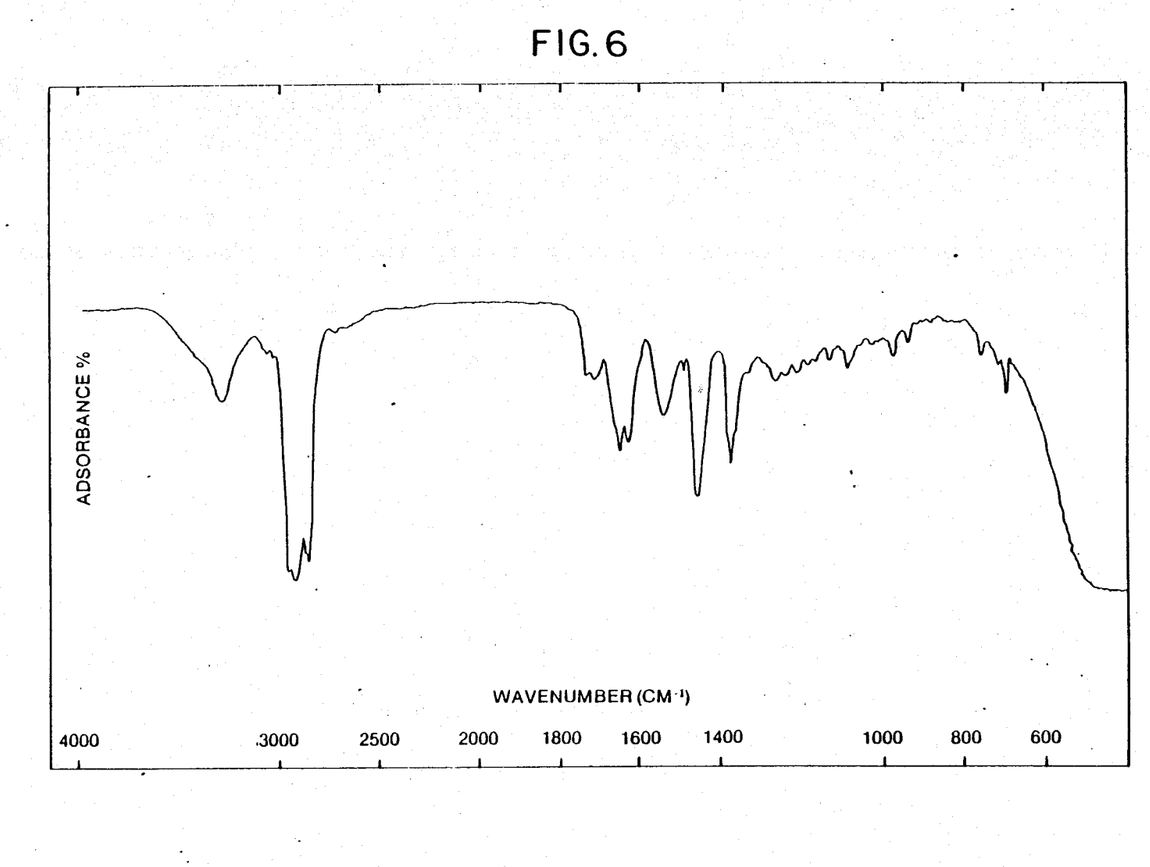

The infrared absorption spectrum in nujol is shown in FIG. 6a of the accompanying drawings. The following absorption maxima (cm$^{-1}$) are observed: 3340, 3295, 3070, 2730, 1720, 1670, 1655, 1630, 1540, 1500, 1270, 1240, 1215, 1190, 1140, 1090, 1040, 980, 945, 760, 720, 700.

The U.V. spectrum shows a terminal absorption at about 215 nm in methanol, (essentially the same as in FIG. 2).

Figure 7:
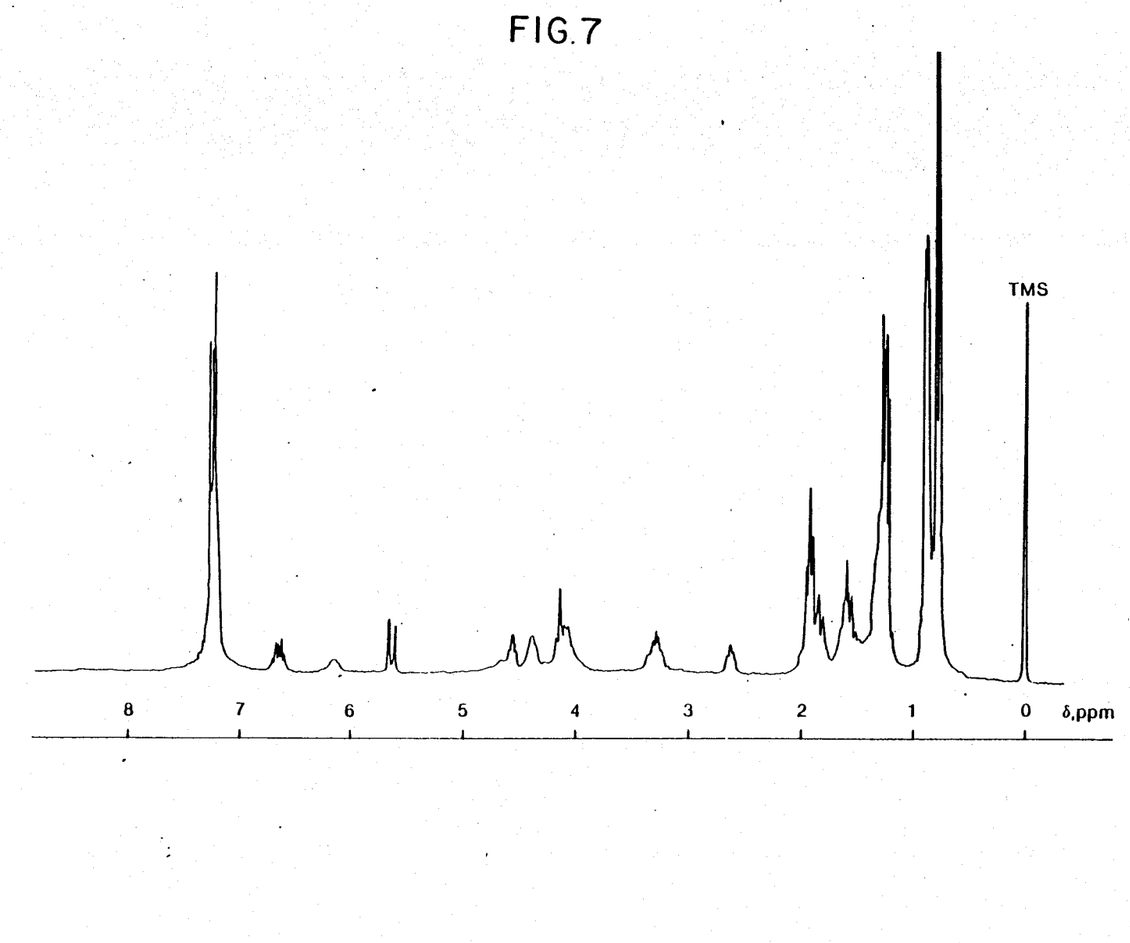

The N.M.R. spectrum, is reported in FIG. 7 and shows the following main peaks: δ0.78 (d, 6H; J=7); 0.87–0.90 (2d, 6H; J=6.5); 1.4–2.0 (m, 8H); 1.24 (d, 3H; J=6.5); 1.27 (d, 3H J=7); 1.92 (ddd, 2H, J=7.5-7.5-1); 2.60 (ddd, 1H, J=2.5-7-11); 3.27 (dq, 1H; J=9); 4.08 (dddd, 1H, J=9; 9-9-2); 4.14 (dd, 1H); 4.38 (ddq, 1H, J=2-11); 4.54 (dd, 1H, J=8); 5.62 (dt, 1H, J=15); 6.13 (d, 1H); 6.60 (dt, 1H); 7.23 (m, 5H); 7.27 (d, 1H).

Figure 8:
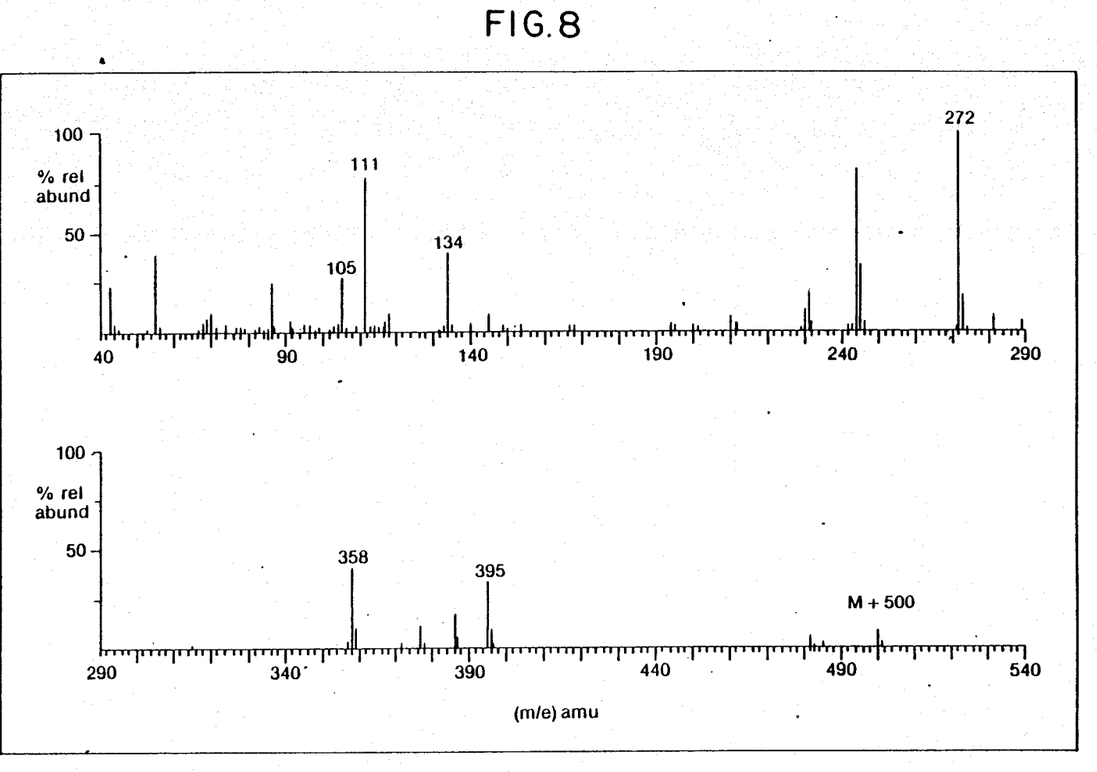

The mass spectrum is reported in FIG. 8. The main peaks are the following (the first number is the rate m/z and the second in parenthesis the the percentage of relative aboundance):

500 (9); 105 (28); 111 (78); 134 (40); 230 (12); 231 (20); 244 (82); 245 (34); 272 (100); 358 (42); 386 (18); 395 (34); 482 (6); 485 (3).

Silica Gel TLC on Merck plate 60 F 254 shows a Rf value of 0.54 when using methylene chloride:methanol, 95:1, and 0.76 when using methylene chloride:methanol, 9:1 as the eluting mixture.

Antibiotic M 9026 factor 3

Antibiotic M 9026 factor 3, is a white crystalline substance with a melting point of about 110° C. (Kofler).

Upon elemental analysis the following approximate percentage composition is obtained: carbon, 67.01%; hydrogen 9.24%; nitrogen, 5.52%; oxygen (by difference), 18.33%.

Figure 9:
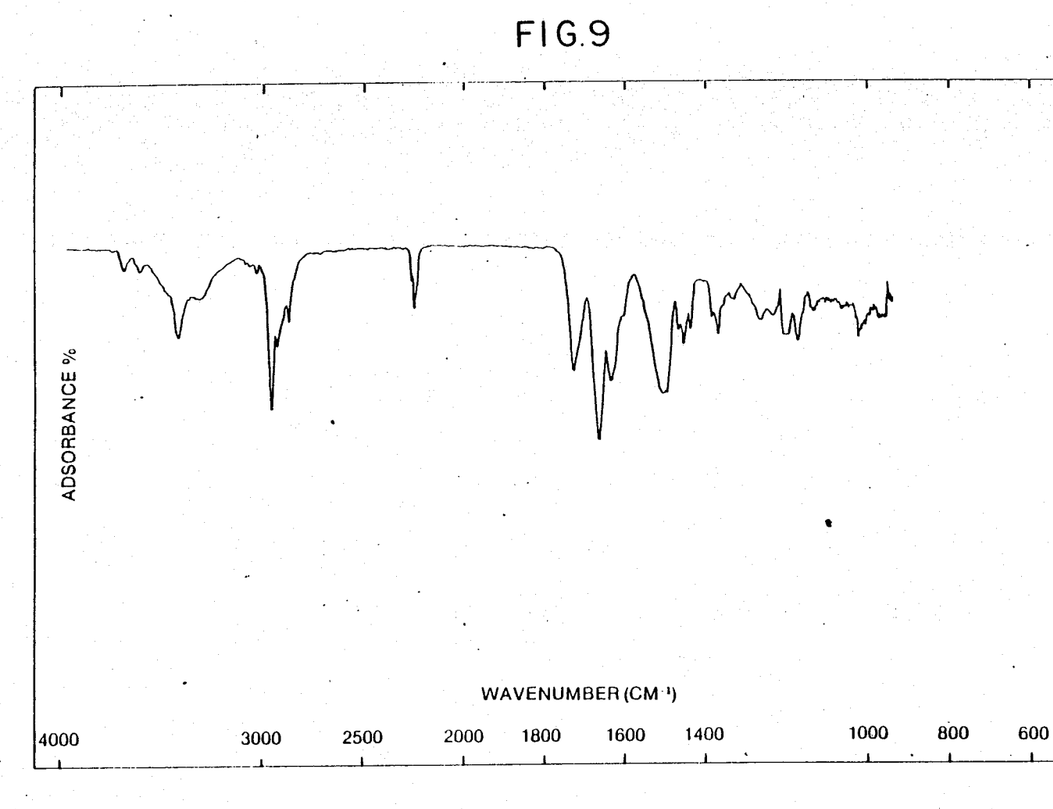

The infrared absorption spectrum in $CDCl_3$ is shown in FIG. 9. The following absorption maxima are shown: 3700, 3610, 3420, 3300, 3040, 2960, 2935, 2880, 1730, 1665, 1635, 1600, 1500, 1455, 1435, 1370, 1275, 1235, 1200, 1170.

The U.V. spectrum shows a terminal absorption at about 215 nm in methanol, (essentially the same as in FIG. 2).

Figure 10:
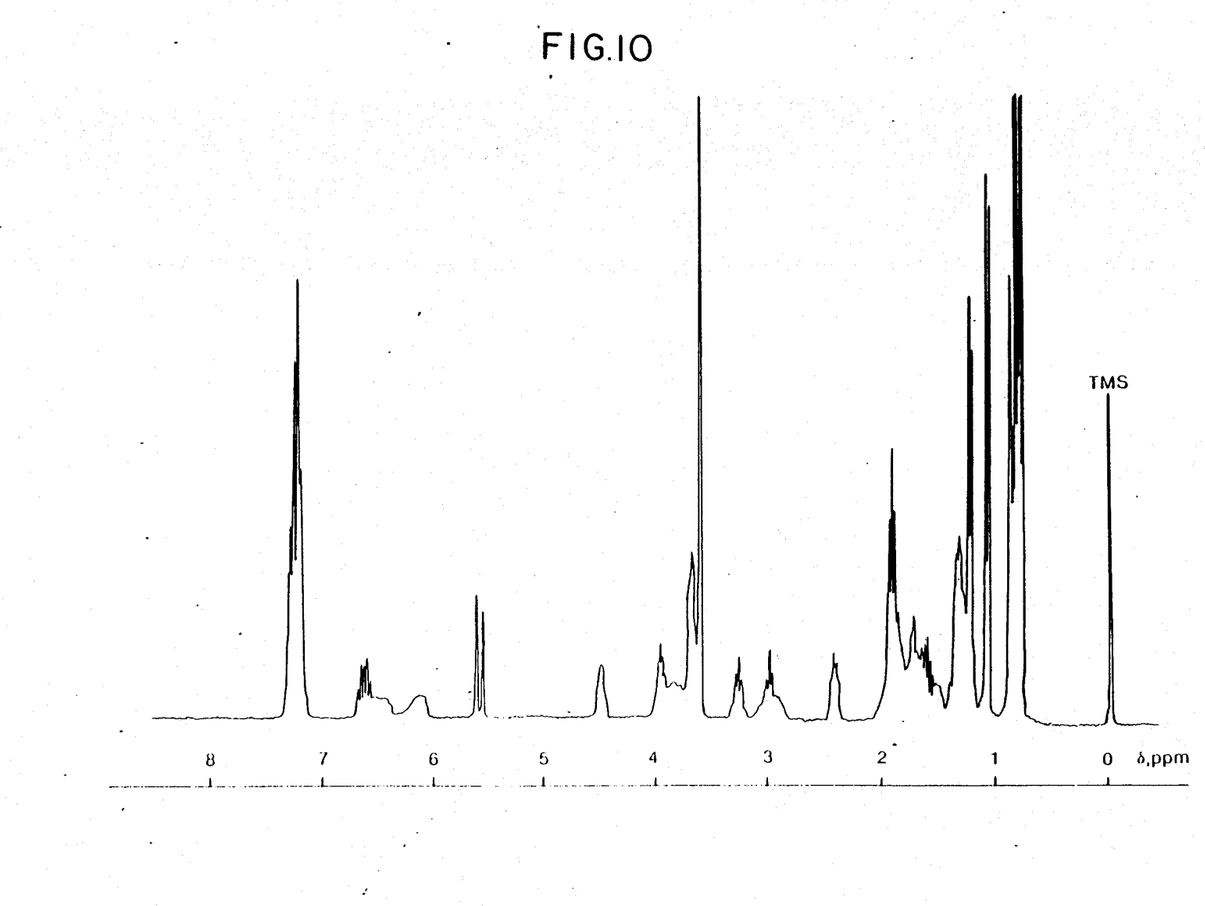

The N.M.R. spectrum is reported in FIG. 10 and shows the following main peaks: $\delta 0.88$ (d, 6H; J=7); 0.91–0.94 (2d, 6H, J=7); 1.4–2.0 (m, 8H), 1.16 (d, 3H; J=6.5), 1.31 (d, 3H, J=7), 1.99 (ddd, 2H, J=7-7-1); 2.49 (ddd, 1H, J=2.5; 7-11); 3.07 (b, 1H); 3.34 (dq, 1H; J=8), 3.68 (S, 3H); 3.70 (m, 1H); 3.75 (dd, 1H, J=10); 3.88 (b, 1H); 4.01 (dddd, J=9, J=2-11); 4.54 (dd., 1H, J=9). 5.62 (dt, 1H, J=15); 6.16 (d, 1H); 6.52 (d, 1H); 6.65 (dt, 1H); 7.27 (m, 5H).

Figure 8A:
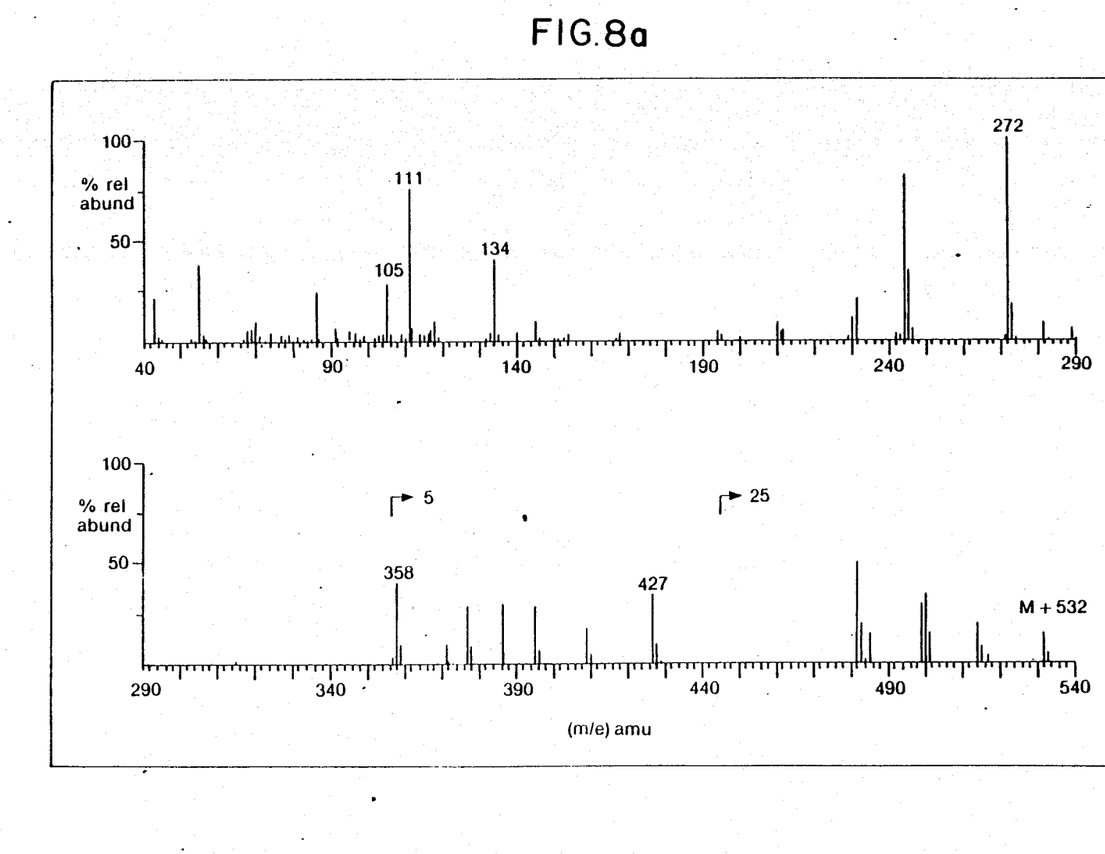

The mass spectrum is reported in FIG. 8a. The main peaks are the following (the first number is the rate m/z, and the second, in parenthesis, is the percentage of relative abundance):

532 (0.6); 105 (28); 111 (76); 134 (40); 230 (12); 231 (20); 244 (82); 245 (34); 272 (100); 358 (40); 386 (6); 395 (5); 427 (7); 482 (2); 500 (1.2).

Silica gel on TLC Merck plate 60 F 254, shows a Rf value of 0.41 when using methylene chloride: methanol, 95:1, and 0.63 when using methylene chloride: methanol, 9:1, as the eluting mixture. Antibiotic M 9026 complex and its factors 1, 2 and 3 possess in vitro antimicrobial activity especially against gram-positive bacteria. In the following table IV, the M.I.C. of antibiotic M 9026 complex are reported. Closely related results are obtained from the single antibiotic M 9026 factor 2 and factor 3.

TABLE IV

| STRAINS | | M.I.C. $\mu g/ml$ |
|---|---|---|
| *Staphylococcus aureus* | ATCC 6538 | 0.1 |
| *Staphylococcus aureus* Tour | | 0.05 |
| *Staphylococcus aureus* Tour (Difco P broth + 30% calf serum) | | 12.5 |
| *Streptococcus haemolyticus* | C 203 | 0.2 |
| *Diplococcus pneumoniae* | UC 41 | 0.4 |
| *Clostridium perfringens* | ISS 30543 | 12.5 |
| *Proteus vulgaris* X 19 H | ATCC 881 | >100 |
| *Pseudomonas aeruginosa* | ATCC 10145 | >100 |
| *Candida albicans* | SKF 2270 | 100 |
| *Trichophyton mentagrophytes* | SKF 17410 | >100 |
| *Mycobacterium tub.* H37Rv | ATCC 9360 | 12.5 |
| *Mycoplasma gallisepticum* H 21 | C.Z.B. | 0.1 |
| *Trichomonas vaginalis* | | >100 |

Antibiotic M 9026 complex and antibiotic M 9026 factor 2, and factor 3 possess cytotoxic activity in vitro as well as antitumor activity in in vivo experiments.

In vitro experiments:

Suspensions of HL60 cells are maintained in RPMI 1640 medium, (see S. J. Collins et al. Nature, 270, 347–349, 1977), supplemented by 20% fetal calf serum, antibiotic (gentamycin 50 μg), 2mM L-glutamine, at 37° C. in a humidified atmosphere with 5% carbon dioxide. The compounds to be tested are dissolved in 10% methanol and then diluted in sterile saline to a final concentration of 1000 μg/ml. The $IC_{50}$ value (i.e. the concentration required for determining the 50% inhibition of the cellular growth with respect to controls) of antibiotic M 9026 complex, was 0.1–0.25 μg/ml. In the same conditions the $IC_{50}$ value for the antibiotic M 9026 factor 2 was 5–0.5 μg/ml, and the $IC_{50}$ value for M 9026 factor 3 was about 0.05 μg/ml, The inhibition of $^3H$-thymidine incorporation is used as a measure of the cell inhibition. Actinomycin D and cycloeximide are employed as a positive control, and show a $IC_{50}$ value of about 0.05 μg/ml and about 0.25 μg/ml, respectively, in the above conditions.

In vivo experiments:

A preliminary screening of the antitumor activity of the compounds of the invention is made with $P_{388}$ tumor-bearing mice. The experiments are carried out essentially following the National Cancer Institute protocols (Geran et al., Cancer Chem. Rep., part III, 3, 17, 1972). In this assay $10^6$ tumor cells are implanted intraperitoneally in $CDF_1$ mice. The test substance is suspended in carboxy methyl cellulose and injected intraperitoneally with a daily treatment from day 1 to 5, starting 24 hours after tumor implantation. Control mice received no compound. Survival time of the treated and control mice are noted and the results obtained in these experiments are expressed as a percentage of control survival-time (T/C):

$$\frac{\text{Median survival time of the treated group}}{\text{Median survival time of the control group}} \times 100$$

A value greater than 100 shows an increase in the median survival time of the treated group as compared to the control group. According to the criteria followed at NCI for the evaluation of the results obtained in this test, a T/C value $\geq 125$ is considered worthy of further study.

At the dosage of 5 mg/kg the T/C value for antibiotic M 9026 complex was 153, and the T/C value for antibiotic M 9026 factor 3 was 168. 5-Fluorouracil was employed as the positive control and showed T/C =168% at the dose of 60 mg/kg.

As stated above, the compounds of the invention possess antimicrobial and antitumor activity. A use of these compounds is therefore as pharmacologically active agents. For this use, the compounds are preferably compounded into the known pharmaceutical compositions suitable for oral or parenteral administration to patients in need. Oral formulations can be in the form of powders, capsules, tablettes, syrups, and the like, and are prepared according to common procedures, and employing adjuvants and carriers well known in the art. For parenteral administration, which is at present the preferred route of administration, the compounds of the invention may be administered as injectable dosages of a solution or suspension of the compounds in a physiologically acceptable carrier which can be a sterile liquid such as water and/or oils, with or without the addition of a surfactant and other pharmaceutically acceptable adjuvants. Illustrative examples of oil which can be employed in these preparations are those of petroleum, animal, or synthetic origin, for example peanut oil, soybean oil, sesame oil, and mineral oil. In general twice distilled, pyrogen-free water, saline, aqueous dextrose and related sugar solutions, ethanol and glycols, such as propylene or polyethylene glycols, can be used as liquid carriers for injectable solutions. These preparations may be used in the form of ready-for-use solutions or preferably in the form of dry soluble products to be combined with the solvent just prior to use. In the latter case the active principle is generally lyophilized. For parenteral administration, the therapeutically effective amount per day is from 0.5 to 20 mg/kg of body weight. Repetitive daily administrations of the compounds may be desired and will vary with the condition of the patient and the mode of administration. The compounds can also be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, a silicone rubber manufactured by the Dow Corning Corporation.

The present invention therefore provides a therapeutic composition including a compound of the invention in an admixture with pharmaceutically acceptable carriers.

The following examples illustrate the manner in which those skilled in the art can practice the invention, but should not be construed as imposing any limitation upon the overall scope of the invention.

The U.V./Vis spectra were recorded using a Perkin-Elmer 320 UV/Vis Spectrophotometer. The mass spectrometry spectra were recorded using a Hitachi-Perkin-Elmer RMU-6L Mass Spectrometer. The N.M.R. spectra were recorded in $CDCl_3$ with TMS as internal standard, using a Bruker WH-270 Spectrometer at 270 MHz.

EXAMPLE 1

Fermentation of the strain Micromonospora sp. NRRL 15,118

A culture of Micromonospora sp. NRRL 15,118 is pre-cultured by growing the strain in a shake flask culture, having the following composition:

| | |
|---|---|
| yeast extract | 5 g |
| beef extract | 3 g |
| tryptone | 4 g |
| dextrose | 1 g |
| starch | 24 g |
| $CaCO_3$ | 4 g |
| tap water q.s. | 1000 ml |

The flasks are kept 48 hours at 30° C. and the pre-culture is used to inoculate jar fermentors each containing 1 liter of the following nutrient medium:

| | |
|---|---|
| yeast extract | 2 g |
| casein hydrolyzate | 4 g |
| beef extract | 2 g |
| dextrose | 10 g |
| starch | 20 g |
| $CaCO_3$ | 3 g |
| tap water q.s. | 1000 ml |

The fermentation batches are incubated under submerged aerobic conditions and stirred at 26°–30° C. The pH is kept between 6.0 and 8.5. At intervals, the antibiotic activity is assayed microbiologically by the agar diffusion method using Staphylococcus aureus as the test organism. The maximum activity is reached after 72 hours.

EXAMPLE 2

Recovery of antibiotic M 9026 complex

The fermentation broth prepared as described in example 1 is filtered. The filtrate is adjusted to pH 7 and extracted twice with an equal volume of ethyl acetate. The organic extracts are pooled and concentrated in vacuo to about 1/100 of the original volume. The precipitate which forms is recovered by filtration. A further amount of the same product is obtained by adding ethyl ether to the mother liquors. After filtration the solid recovered is dried in vacuo at room temperature, thus obtaining the crude antibiotic M 9026 complex.

EXAMPLE 3

Recovery of antibiotic M 9026 factor 1

The mycelial mass obtained by filtering the fermentation broth is washed with water, the pH is adjusted at about 7.0, and the mixture is suspended in methanol while stirring for 20 minutes. Then, the mixture is filtered and the methanol is stripped out from the filtrate. The obtained aqueous layer is adjusted to pH 7.0 and extracted with ethyl acetate as described above for the fermentation broth. The obtained antibiotic M 9026 factor 1 can be purified as described for M 9026 factor 2, and factor 3 (see example 4). Its physico-chemical characteristics are as disclosed above.

Similar results are obtained by substituting ethyl acetate with chloroform or methylethylketone in the above procedure.

EXAMPLE 4

Purification of antibiotic M 9026 complex 1.5 g of crude complex (obtained according to example 1 a), are dissolved in 10 ml of the eluting mixture and applied to a silica gel chromatography column. Kieselgel 60 (70–230 mesh ASTM) (120 g) Merck, prepared in chloroform: methanol: ammonia 66:30:4. The column is developed using cloroform: methanol: ammonia mixture (60:30:4) and collecting 15 ml fractions. Elution of the column is monitored by assaying each fraction against HL 60 cells, or Staphylococcus aureus, or B. subtilis and by thin layer chromatography bioautography, using S. aureus as the detecting organism. The fractions are combined according to the activity exhibited. Ethyl ether is added to the concentrated combined fractions to precipitate the purified antibiotic M 9026 complex. Isopropyl ether or, petroleum ether can also be used in this last step. The physico-chemical characteristics of this product are as disclosed above.

EXAMPLE 5

Separation of antibiotic M 9026 factor 2 and factor 3.

Purified M 9026 complex (340 mg), obtained as described in example 4, is dissolved in 5 ml of methylene chloride:methanol, 9:1. The resulting solution is applied to a 30 g silica gel chromatography column Kieselgel (70–230 mesh ASTM) Merck, prepared in methylene chloride: methanol, 9:1. The same mixture is used to develop the column, collecting 15 ml fractions. Elution of the column is monitored by assaying fractions against Staphylococcus aureus, or B. subtilis HL 60 cells, or by TLC or TLC-bioautography using *S. aureus* or *B. subtilis* as the detecting organisms. Fractions are combined according to the factor content and the activity exhibited. Each combined fraction is concentrated in vacuo. Each concentrate is added to ethyl ether to precipitate the desired factor. Following this procedure, three major factors are separated subsequently and called factor 2 and factor 3 respectively.

Their physico-chemical characteristics are as reported above.

We claim:

1. Antibiotic M 9026 complex obtainable by culturing the strain Micromonospora sp. NRRL 15,118, or M 9026 complex producing mutants thereof, under submerged aerobic conditions, in an aqueous nutrient medium containing assimilable sources of carbon, nitrogen and inorganic salts until substantial M 9026 complex activity is imparted to the culture medium, filtering the fermented medium, extracting the antibiotic M 9026 complex from the filtrate, causing the antibiotic M 9026 complex to precipitate from the extract, and collecting the solid precipitate, wherein the antibiotic M 9026 complex has the following infrared absorption maxima $(cm^{-1})$: 3260 (broad), 3060, 2730, 1735, 1720 (shoulder), 1650, 1630, 1545, 1515, 1495, 1300, 1260, 1210, 1170, 1090, 1030, 980, 940, 830, 760, 720, 700; and has an ultraviolet terminal absorption in methanol at 215 nm.

2. Antibiotic M 9026 complex obtainable by culturing the strain Micromonospora sp. NRRL 15,118, or M 9026 complex producing mutants thereof, under submerged aerobic conditions, at 26°-30° C., at a pH of 6.0-8.5, until a substantial amount of M 9026 complex activity is imparted to the culture medium, and recovering said antibiotic complex by extracting the fermentation broth with an organic solvent selected from the group consisting of lower alkanols, halo-lower alkanes, lower alkyl esters, and lower alkyl ketones, wherein the antibiotic M 9026 complex has the following infrared characteristics: 3260 (broad), 3060, 2730, 1735, 1720 (shoulder), 1650, 1630, 1545, 1515, 1495, 1300, 1260, 1210, 1170, 1090, 1030, 980, 940, 830, 760, 720, 700, and having an ultraviolet terminal absorption in methanol at 215 nm.

3. Antibiotic M 9026 factor 1 which is a crystalline solid characterized by:
(a) melting pint of 235° C.;
(b) good solubility in chloroform and methanol, limited solubility in acetone and hydrocarbons, and insolubility in water;
(c) elemental analysis percentage composition: carbon, 68.83%; hydrogen, 8.70%; nitrogen, 5.56%; oxygen (by difference), 16.91%;
(d) infrared absorption maxima $(cm^{-1})$ in nujol 3670, 3550, 3460, 3320, 3100, 3080, 3040, 2740, 1720, 1660, 1630, 1545, 1500, 1260, 1245, 1220, 1190, 1140, 1090, 1040, 985, 950, 895, 750, 725, 700;
(e) ultraviolet absorpiton spectrum: a terminal absorption at 215 nm in methanol;
(f) N.M.R. main peaks ($\delta$=ppm; J=Hz): $\delta$0.70-0.73 (2d, 6H, J=6.5), 0.83 (d, 6H, J=7), 1.0-2.0 (m, 4H), 1.06 (m, 1H), 1.24 (d, 3H, J=6.5), 1.5-2.0 (m, 2H), 1.66 (t sept, 1H, J=7.5), 1.98(ddd, 2H J=7.5-7.5-1); 2.49 (ddd, 1H, 1H, J=7-10; 2.5), 3.00 (d,2H; J=7.5), 3.91 (dddd, 1H, J=9; 8; 2.5-9.5), 4.08 (dd, 1H), 4.32 (ddq, 1H; J=2.5-10), 4.57 (dt, 1H; J=8), 5.69 (dt, 1H J=15), 6.15 (d,1H), 6.22 (d, 1H), 6.73 (dt, 1H), 7.18 (m, 5H); and (g) mass spectrum main fragmentation peaks: m/z (percentage of base peak) 486 (35); 91 (18); 111 (81); 120 (37); 216 (18); 217 (19); 230 (70); 231 (34); 258 (100); 344 (48); 372 (8.3); 395 (3.5); 486 (2.6); 471 (1.1).

4. Antibiotic M 9026 factor 2 which is a white-grey powder characterized by:
(a) melfing point above 280° C.;
(b) good solubility in methanol, efhanol, acetone, ethyl acetate and chloroform; spare solubility in acetonitrile, insolubility in water, petroleum ehter, or ethyl ehter;
(c) elemental analysis percentage composition: carbon, 68.82%; hydrogen, 9.04%; nitrogen, 5.70%; oxygen (by difference), 17.09%;
(d) infrared absorption maxima $(cm^{-1})$ in nujol: 3340, 3295, 3070, 2730, 1720, 1670, 1630, 1540, 1500, 1270, 1240, 1215, 1190, 1140, 1090, 1040, 980, 945, 760, 720, 700;
(e) ultraviolet spectrum: a terminal absorption at about 215 nm in methanol;
(f) N.M.R. main peaks ($\delta$=ppm; J=Hz) $\delta$0.78 (d, 6H; J=7); 0.87-0.90 (2d, 6H, J=6.5); 1.4-2.0 (m, 8H); 1.24 (d, 3H; J=6.5); 1.27 (d, 3H; J=7); 1.92 (ddd, 2H, J=7.5-7.5-1); 2.60 (ddd, 1H, J=2.5-7-11); 3.27 (dq, 1H; J=9); 4.08 (dddd, 1H, J=9; 9-9-2); 4.14 (dd, 1H) 4.38 (ddq, 1H, J=2-11); 4.54 (dd, 1H, J=8); 5.62 (dt, 1H, J=15); 6.13 (d, 1H); 6.60 (dt, 1H); 7.23 (m, 5H); 7.27 (d, 1H);
(g) mass spectrum main fragmentation peaks: m/z (percentage of base peak) 500 (9); 105(28); 111 (78); 134 (40); 230 (12); 231 (20); 244 (82); 245 (34); 272 (100); 358 (42); 386 (18); 395 (34); 482 (6); 485 (3); and
(f) Rf values on TLC Merck plate 60 F 254: 0.54 in methylene chloride:ethanol, 95:1, and 0.76 in methylene chloride:methanol, 9:1.

5. Antibiotic M 9026 factor 3, which is a white crystalline substance characterized by:
(a) melting point of 110° C. (Kofler);
(b) elemental analysis percentage composition, carbon, 67.01%; hydrgoen, 9.24%; nitrogen, 5.52%; oxygen (by difference), 18.33%;
(c) infrared abosorption maxima $(cm^{-1})$ in CDCl$_3$: 3700, 3610, 3420, 3300, 3040, 2960, 2935, 2880, 1730, 1665, 1635, 1600, 1500, 1455, 1435, 1370, 1275, 1235, 1235, 1200, 1170;
(d) ultraviolet spectrum: a terminal absorbption at about 215 nm in methanol;
(e) N.M.R. main peaks ($\delta$=ppm; J=Hz): $\delta$0.88 (d, 6H; J=7); 0.91-0.94 (2d, 6H, J=7); 1.4-2.0 (m, 8H), 1.16 (d, 3H; J=6.5), 1.31 (d, 3H, J=7), 1.99 (ddd, 2H, J=7-7-1); 2.49 (ddd, 1H, J=2.5; 7-11); 3.07 (b, 1H); 3.34 (dq, 1H; J=8), 3.68 (s, 3H); 3.70 (m, 1H); 3.75 (dd, 1H, J=10); 3.88 (b, 1H); 4.01 (dddd, J=9, J=2-11); 4.54 (dd, 1H, J=9). 5.62 (dt, 1H, J=15); 6.16 (d, 1H); 6.52 (d, 1H); 6.65 (dt, 1H); 7.27 (m, 5H);
(f) mass spectrium main fragmentation peaks: m/z (percentage of base peak) 532 (0.6); 105 (28); 111 (76); 134 (40); 230 (12); 231 (20); 244 (82); 245 (34); 272 (100); 358 (40); 386 (6); 395 (5); 427 (7); 482 (2); 500 (1.2); and
(g) Rf values on TLC Merck plate 60 F 254 0.41 in methylene chloride:methanol, 95:1, and 0.63 in methylene chloride: methanol, 9:1.

6. A process for producing antibiotic M 9026 complex which comprises culturing the strain Micromonospora sp. NRRL 15,118, or M 9026 complex producing mutants thereof, under submerged aerobic conditions, in an aqueous nutrinet medium containing assimilable sources carbon, assimilable sources~ of nitrogen, and inorganic salts until substantial M 9026 complex activity is imparted to the culture medium, filtering said fermentation medium, extracting the anti-biotic M 9026 complex from the filtrate, causing the antibiotic M 9026 complex to precipitate from the extract, collecting the solid precipitate, and isolating factor 1, factor 2, and factor 3 from the antibiotic M 9026 complex via silica gel chromatography.

7. A process as in claim 6 wherein the fermentation is carried out at a temperature between 26° and 30° C.

8. A process as in claim 6 wherein the fermentation is carried out at a pH between 6.0 and 8.5.

9. A process as in claim 6, wherein the antibiotic is recovered at the end of the fermentation by extraction of the filtrate with an organic solvent selected from the group consisting of lower alkanols, halo lower alkanes, lower alkyl esters, and lower alkyl ketones.

10. A process as in claim 6, wherein the antibiotic is recovered at the end of the fermentation by extraction of the filtrate with an organic solvent selected from the group consisting of lower alkanols, halo lower alkanes, lower alkyl esters, and lower alkyl ketones, after having adjusted the pH of the filtrate between 3.5 and 8.5.

11. A process as in claim 6, wherein the antibiotic is recovered at the end of the fermentation by extraction of the filtrate with an organic solvent selected from the group consisitng of lower alkanois, halo lower alkanes, lower alkyl esters, and lower alkyl ketones, after having adjusted the pH of the filtrate between 6.0 and 7.5.

12. A process as in claim 6, wherein the antibiotic is recovered at the end of the fermentation by extraction of the filtrate with ethyl acetate.

13. A process as in claim 6 wherein antibiotic M 9026 factor 2 and factor 3 are separately isolated by chromatography.

14. A process as in claim 26 wherein antibiotic M 9026 factor 2, or factor 3 are isolated by column chromatography using a silica gel column and eluting with a mixture of methylene chloride: methanol, 9:1 (v/v).

15. A biologically pure culture having the identifying characteristics of Micromonospora sp. NRRL 15,118.

16. A biologically pure culture of the microorganism Micromonospora sp. NRRL 15,118 or equivalent mutants thereof, capable of producing antibiotic M 9026 in a recoverable amount upon aerobic fermentation in an aqueous nutrient medium containing assimilable sources of carbon, nitrogen, and inorganic salts.

17. A pharmaceutical composition which comprises a compound or a mixture of compounds selected from the group consisting of antibiotic M 9026 complex, antibiotic M 9026 factor 2, and antibiotic M 9026 factor 3, and mixtures thereof in admixture with a pharaceutically acceptable carrier.

18. A pharmaceutical composition according to claim 17, wherein the compounds are antibiotic M 9026 factor 2 and antibiotic M 9026 factor 3.

* * * * *